(12) United States Patent
Abdelrahman

(10) Patent No.: US 6,521,452 B1
(45) Date of Patent: Feb. 18, 2003

(54) SUGAR CANE PRODUCTION

(75) Inventor: Layla Zakaria Abdelrahman, 297 Parrs Wood Road, Didsbury, Manchester M2O 6JZ (GB)

(73) Assignee: Layla Zakaria Abdelrahman (GB)

( * ) Notice: Subject to any disclaimer, the term of this patent is extended or adjusted under 35 U.S.C. 154(b) by 0 days.

(21) Appl. No.: 09/377,941

(22) Filed: Aug. 20, 1999

(30) Foreign Application Priority Data

Feb. 21, 1997 (GB) ............................................. 9763628
Feb. 20, 1998 (GB) ............................. PCT/GB98/00387

(51) Int. Cl.$^7$ ............................ A01H 4/00; C12N 5/00; C12N 5/02; C12N 5/04
(52) U.S. Cl. .................... 435/420; 435/430.1; 435/431; 435/410; 800/320; 800/295; 47/57.6; 47/58.1
(58) Field of Search ............................. 435/420, 430.1, 435/431, 410; 800/320, 295; 47/57.6, 58.1

(56) References Cited

U.S. PATENT DOCUMENTS 4,562,663 A * 1/1986 Redenbaugh ................ 47/57.6
5,427,593 A * 6/1995 Carlson et al. .............. 47/57.6

OTHER PUBLICATIONS

Ahloowalia and Maretzki, Plant Cell Reports (1983) 2:21–25.*
Ho and Vasil, Ann. Bot., 51, 719–726, 1983.*
*Plant Cell Biotechnology*, Endress, R., ed., Springer–Verlag (Berlin: 1994), p. 110.
C.H. Bornman in *Synseeds*, Redenbough, K., ed., Chapter 6 "Maturation Of Somatic Embryos", CRC Press (Boca Raton: 1993), p. 105–113.
Taylor et al., "Establishment of Embryonic Callus and High Protoplast Yielding Suspension Cultures of Sugarcane," *Plant Cell, Tissue and Organ Culture*, 28:69–78 (1992).
*Plant Biochemistry*, P.M. Dey & J.B. Harbone, eds., Academic Press (San Diego, California: 1997), Chapter 15.2 "Plant Cell Culture", at pp. 518–519.
*Glossary of Plant Tissue Culture*, Donnelly, D.J. and Vidaver, W.E., Belhaven Press (London: 1988), p. 15.
J.J. Finer, Chapter 5 "Plant Regeneration via Embryogenic Suspension Cultures," in *Plant Cell Culture: A Practical Approach*, Dixon, R.A. and Gonzales, R.A., eds., Oxford University Press, (Oxford: 1994), p. 110–112.
I.K. Vasil, "Somatic Embryogenesis and its Consequences in the Gramineae," in *Tissue Culture in Forestry and Agriculture*, Henke, R. et al., eds., Plenum Press (New York: 1984), pp. 31–47.

* cited by examiner

Primary Examiner—Bruce R. Campell
Assistant Examiner—Anne Marie Grunberg
(74) Attorney, Agent, or Firm—Welsh & Katz, Ltd.; Thomas W. Tolpin

(57) ABSTRACT

Plants, particularly sugar cane plants, are reproduced using explant material which may be derived from leaves, shoots, roots and other plant parts. Somatic embryos are produced by culturing immature embryos from the explant material and then culturing mature, somatic embryos from the immature embryos. All achieved in liquid suspension culture, which allows micro propagation of sugar cane without the culture suffering, browning at any stage. The mature embryos can then be encapsulated to form artificial seeds for germination purposes.

49 Claims, No Drawings

SUGAR CANE PRODUCTION

This invention relates to sugar cane plants and more particularly to methods of producing such plants.

Sugar cane is well known as an extremely important crop plant because of its use in the production of foodstuffs and the use of its by-products such as molasses, bagasse, filter mud and ethanol, all of which are of great value to both developing and developed countries.

Generally, sugar cane is cultivated as a perennial crop. The plant is allowed to grow for one year and is known as "plant cane". The plant cane is cut at this stage and processed to produce sugar. The plant cane root and a small amount of cane stem is left in the ground and this grows over the next year to produce the "first ratoon". This is then harvested to produce sugar and the residue of the plant is left to grow for a further year to produce the "second ratoon". In some countries this growing cycle is repeated up to a "fifth ratoon" before the plant is finally uprooted.

Sugar cane is wind-pollinated and this leads to great variability in the plants obtained from seeds. This is useful for breeding programmes because it produces many different plant variations which can be used to select new useful clones. However, for normal commercial propagation the natural reproductive method does not give true-to-type plants. As a result, up until now, vegetative propagation has been the only practical means of propagating sugar cane. The existing method of propagating sugar cane relies on using the stems of mature sugar cane. This method is very wasteful in terms of reducing the overall productivity of the sugar cane crop, is expensive in terms of labour costs and can also produce problems in terms of spreading virus diseases such as Fiji disease, bacterial diseases such as red rot and the main fungal disease of smut. Disease problems in sugar cane production can be extremely serious since they are spread by many different vectors and can very rapidly spread throughout sugar cane plantations.

Unfortunately, vegetative propagation is very expensive because the plant has to grow for 9–12 months before the stem can be cut down into segments of about 30 cm. The main problem is that the cut ends of the cane are exposed to contamination, especially due to the presence of the nutrient sucrose in the cane sap. As a result, it is easy to spread viral, bacterial and fungal diseases which can have serious effects on sugar cane production.

Because of all these problems with the production of new sugar cane plants, tissue culture methods have been developed for breeding and propagation programmes and for the elimination of viruses. For example, Barredo R., Luzaman R and Dequinto B. (1994) used the spindle leaf (the innermost leaf of the tiller) to produce 13,500 plantlets from variety Phil 74–64. However, they found that it took 8 months from the beginning of the laboratory work to produce seedlings capable of being planted in the field. Barba R. C., Zamora A. B., Linga C. K. and Thai Van N. (1975) used a callusing method which allowed them to produce 4,000 plantlets from a 3 cm piece of sugar cane shoot but disadvantageously this method can lead to genetic variations.

Recent advances in biotechnology have offered new opportunities for crop improvement and propagation through plant tissue culture techniques.

Somatic embryos are bipolar structures which contain both shoot and root meristems. They may be formed in both callus and cell suspension culture and lead directly to the formation of mature plants. Somatic embryogenesis offers a potential system for large scale production of plants. However, for somatic embryogenesis to be practical for the large scale production of plants, numerous problems have to be overcome which, up until the present invention, have remained obstacles to the use of the method for the production of sugar cane plants. Up until the present invention, mature somatic embryos have only been produced from callus grown on solid medium. Cells grown in callus are known to be genetically unstable and so the embryos grown from callus are likely to be genetically distinct. Moreover, callus-derived embryos do not grow in synchrony and manipulation is labour-intensive. Such problems render callus-derived somatic embryogenesis unsuitable for large-scale commercial propagation. By contrast, cell suspensions in liquid culture show greater genetic stability, can be synchronised by modifying growth conditions and can be subjected to automated manipulation. Up until the present invention, attempts at liquid culture only succeeded in producing immature globular embryos.

The present invention has been provided through a consideration of the above mentioned problems. The present invention addresses those problems and provides an efficient and reliable method of producing sugar cane plants which is particularly suitable for use on a large scale for commercial purposes.

According to the present invention there is provided a method of producing sugar cane somatic embryos from sugar cane explants comprising the steps of:

(1) culturing immature embryos from explants
(2) culturing mature sugar cane somatic embryos from those immature embryos The present invention provides a system involving somatic embryogenesis for the production of somatic embryos for use in the production of sugar cane plant as mature somatic embryos may be produced quickly and in large quantities and the original plant gene characteristics are maintained in the somatic embryos.

The sugar cane somatic embryos produced by the method of the present invention may subsequently be germinated to produce sugar cane plants or may be encapsulated in an encapsulating agent to produce "artificial seeds" for direct delivery to the field for subsequent germination of the embryos in situ.

Most preferably at least step 2 occurs in liquid suspension culture as this is the most practical media for use of the method on a large scale.

The production of sugar cane somatic embryos by the method of the present invention involves somatic embryogenesis. This method is extremely valuable because it is possible to produce vast numbers of embryos in small volumes of culture media in an approximately synchronous manner. A high multiplication rate, however, is only the first of several potential advantages offered by somatic embryogenesis for the subsequent production of sugar cane plants in comparison with other methods of vegetative propagation of sugar cane plants. For example, both the growth of embryogenic tissue in step (1) and the subsequent development of the embryos to maturity in step (2) can be accomplished in liquid medium, making possible the manipulation of very large numbers of propagules with minimal handling. In addition, the product of somatic embryogenesis is an embryo that is capable of developing into a regenerated sugar cane plant with very little further input of labour. The advantage of somatic embryogenesis for the production of sugar cane plants over the prior art systems of vegetative propagation and micro-propagation is the presence of both root and shoot meristems in the same unit and therefore there is no requirement for the laborious transfer operations, thus reducing operating costs very significantly.

In addition, this absence of repetitive transfer operations advantageously decreases contamination which is spread by contact. A further advantage is that the embryogenic systems are capable of producing separated individual embryos, unattached to either mother tissue or other embryos. Thus, embryogenic cultures produce propagules that are not only complete but also discrete. The combination of those-two properties gives somatic embryos potential for direct delivery to the greenhouse or field for example, as components of artificial seeds or in a fluid drilling system.

The method of the present invention advantageously provides an in vitro multiplication tool providing the new possibility of quickly obtaining large quantities of sugar cane embryos in a liquid medium. This permits much greater and faster propagation of sugar cane plants than can presently be obtained using other techniques, such as micropropagation, which suffer from high labour costs.

Sugar cane plants, regenerated using the method of the present invention which involves somatic embryogenesis, are most preferably derived from characteristic organised meristems or meristematic cells of sugar cane plants. These cells are by nature genetically stable and not prone to mutational changes. Indeed, there is evidence that there is strong selection in favour of genetically normal cells during somatic embryo development. Consequently, sugar cane plants derived from the method of the present invention give rise to truly clonal populations which is important for the reliable and efficient mass production of sugar cane plants.

Embryogenic suspension cultures are particularly suitable for large scale production because of the absence of repetitive handling of the plant tissue, the potential to easily scale-up the process and the relative ease of automating the process. The development of the process into a practical production system requires, ideally, that single embryos are produced, that the embryos are at the same stage of development and that there is ultimately a high conversion rate into seedlings. The advantage of using embryos as propagules is that it is possible to encapsulate them for direct delivery to the field.

Furthermore the method of the present invention advantageously provides means by which the sugar cane plants can be regenerated from cells which have been selected in manipulated cultures. Accordingly, the method of the present invention provides an efficient method for use in sugar cane novel genetic manipulation techniques for crop improvement, such as somatic hybridization and genetic transformation.

The explant used in step 1 of the method of the present invention may be taken from any part of and at any stage of development of a sugar cane mother plant. For example, the source of explant can be from the leaf, root, young shoot, buds, infloresence, young intemodes of the sugar cane plant and/or the explants may comprise mature embryos derived by stressing leaf, young shoot, root, buds, infloresence or young intemodes of the sugar cane plant. Stressing may be achieved by treating the plant part with 95% ethanol for a period of time (preferably 1–5 hours) and/or cooling the plant part to a temperature of approximately 5–15° C. for approximately 1–3 months. Most preferably root-derived or mature embryos are used as the explant material.

Root explant is advantageously most productive in forming immature embryos, which is probably due to the root (particularly the tip) consisting mainly of meristematic tissues. Furthermore, root explant advantageously is less affected by the known problem of "browning" of culture media and cells in plant tissue culture techniques. The "browning" effect is produced by the oxidation of phenolic compounds to quinone oxidation products; Phenolic derivatives are often released by explants. Since browning of the immature embryo culture when derived from root explants is substantially absent, advantageously there is no need to change the culture medium and accordingly, root-derived cultures tend to accumulate more bio-mass over any fixed period of time.

A further advantage of using root-explant rather than leaf or shoot explants is that a fine, highly dispersed immature embryo culture is generated. Moreover, root explants may be used to generate embryos in liquid suspension culture directly, without the need for the formation of intermediate callus and without the need to change the culture media every 2 to 5 days. This feature is very important for the application of the method of the present invention industrially as a means of propagation of sugar cane using somatic embryogenesis. Culture of root explant together with non-root explant confers substantially the same advantages on the mixed culture as those above described advantages for root explant culture alone. For example, where "browning" would normally occur in shoot-explant culture, such browning is minimized in a mixed shoot and root explant culture.

Furthermore, root explants are readily available since roots are easily induced by placing shoot material, including at least one node, in distilled water. After a period of time, a root network grows, from which explant material may be sourced. This is particularly useful in the industrial application of the method of the present invention.

The advantages of using leaf explant include their ready availability and that they may usually be sourced in an uncontaminated state.

Where leaf explants are used, most preferably the leaf explant is sourced from an area close to the growing point of the plant since the frequency of browning of the culture medium increases with increasing distance from the growing point. Furthermore, the age of the donor plant from which the leaf explant is sourced is preferably between approximately 3–12 months, but most preferably approximately 9 months as the frequency of browning of the culture media is substantially absent and virtually all leaf segments from a 9 month old plant are highly embryogenic.

The above mentioned advantages of using root explant, alone or in combination with other sources of explant, and in particular for the avoidance of the frequently encountered problems of "browning" in plant culture techniques, are beneficial for culture of all types of plants (such as trees, date palm, potatoes) and accordingly use of sugar cane root explant is not limited to the culture of sugar cane. The method of culturing immature embryos from explants (step 1 of the present invention) preferably comprises the steps of:

(a) culturing explant material on culture medium to produce somatic cells (b) selecting and multiplying somatic cells derived from the explant material (c) culturing the somatic cells for a period of time on culture medium to induce immature sugar cane embryos from the somatic cells The immature embryos may be initiated and maintained as embryogenic callus on solid media or as an embryogenic cell suspension culture in liquid media or on a combination of both solid and liquid media preferably as a "double layer" medium.

A wide range of solid and/or liquid culture media may be used in the method of the present invention from relatively dilute media to the more concentrated formulations of Evans et al, Gamborg et al, Schenk and Hildebrandt (SH medium) and Murashige and Skoog (MS medium). Most preferably solid or liquid MS medium is used for the. method of the present invention as it is particularly advantageous for formation of immature embryos as embryogenic callus/suspension culture and for the induction of somatic embryogenesis thereof possibly due to the presence of higher levels of ammonia nitrogen in MS medium. Different media may be used in the different steps of the method of the present invention as required.

Most preferably plant growth regulators such as auxins (eg 2,4-dichlorophenoxyacetic acid (2,4-D), naphthaleneacetic acid (NAA), indole 3-acetic acid (IAA)), cytokinins, gibberellins, abscissic acids anti-auxins, kinetin, zeatin and/or activated charcoal are included either alone or in combination in the media formulation. 2,4-D auxin is the most effective regulator for the induction of immature embryo (callus formation and/or suspension culture) development from explants and for the development of somatic embryos from the immature embryos in the method of the present invention. A wide range of concentrations of 2,4-D are suitable, for example 0.5–10 mg/l, but most preferably a relatively high concentration is used such as approximately 3–5 mg/l. In contrast, cytokinins have an inhibitory effect on the growth of immature sugar cane embryos. Preferably ABA is included together with 2,4-D in the culture media, at a concentration of 0.1–20 mg/l and most preferably at a concentration of approximately 1 mg/l. ABA advantageously retards the growth of non-embryogenic cells so that the percentage of embryogenic cells in culture is optimized.

As carbon and energy sources, carbohydrates are a major and essential constituent of a tissue culture medium. Most preferably sucrose is used as the major carbohydrate constituent of the media used in the method of the present invention for the culture of sugar cane. Many other monosaccharide, such as glucose and fructose, disaccharides such as lactose and other sugars such as melibiose can also support growth and embryogenesis in the culture method of the present invention. However, the use of sucrose is particularly advantageous for the method of the present invention as it does not increase culture browning. The concentration of sucrose used is preferably in the range 10–60 g/l. Most preferably the concentration of sucrose used is approximately 30 g/l. Up until the present invention it has been usual in the culture of sugar cane for coconut water to be a constituent of the culture medium. However, advantageously in the method of the present invention coconut water is not a required constituent, thus reducing costs.

The production of embryogenic callus and/or embryogenic suspension culture is most effectively stimulated by stressing the explant material and/or the tissue from which the explant material is sourced prior to introduction of the explant material to the medium (step a).

For example, this be may achieved by a stress-treatment involving cooling the explants to a temperature of approximately 5° C.–15° C. for approximately 1–3 months. Most preferably the explants are cooled to approximately 10° C. for approximately 2 months. Other suitable stress-treatments to stimulate embryo production include soaking the explants in approximately 95% ethanol for approximately 1–5 hours. The latter ethanol method is preferred as this is a ready method of treating sugar cane explants to remove contamination whilst leaving the cells viable for culture to form embryonic material. The most preferable time period for soaking the explants in ethanol is approximately 4 hours.

Preferably the exposed cut ends of tissue donated from the mother sugar cane plant are coated with wax, such as candle wax, prior to ethanol treatment to reduce the absorption of ethanol by the tissue exposed at the cuts. After soaking the tissue in ethanol preferably the tissue is wrapped in sterilized dry tissue paper or the like to absorb the surplus ethanol. Explant material may then be selected and dissected from the donor tissue (eg leaf, shoot, root) and introduced to the culture medium. The explant is then cultured for a period of time to induce the formation of somatic cells. Somatic cell development is most preferably positively selected by using a culture medium which comprises ABA. ABA retards the growth of other types of cells so optimizing the percentage of the desired somatic cells. Somatic cells are further selected by a method which separates cells according to their size and shape. Sugar cane somatic cells are typically rounded in shape having a diameter of approximately 40–65 $\mu$m and most typically between 46–63 $\mu$m. In contrast non-embryogenic sugar cane cells are typically elongate and less than approximately 46 $\mu$m in length. A convenient method of selecting substantially only somatic cells is to sieve the culture through a first sieve of 100–50 $\mu$m mesh size, which thus substantially allows somatic and non embryogenic cells to pass through (but collects any larger particles such as cell aggregates), and then subsequently to sieve that sieved culture through a second sieve having a mesh size of 50–38 $\mu$m and which substantially allows non-embryogenic cells to pass through whilst substantially collecting the somatic cells. Optimal selection of somatic cells occurs where the first sieve is around 63 $\mu$m and the second sieve is around 45 $\mu$m.

The selected somatic cells are then preferably resuspended in the above described 2,4D containing media, which preferably also contains ABA as above described, for multiplication purposes.

The somatic cells are then cultured for a period of time to form immature embryos, step (c). Generally the time period is between 10 and 40 days depending upon, for example, the nature of the explant, culture media used and concentration and type(s) of growth regulators used. Generally, the percentage of somatic cells forming immature embryos increases with the concentration of 2,4-D.

Immature embryos may be produced by the method of the present invention in dark or light conditions or a combination of both dark and light conditions. Most preferably the culture is exposed to photo period cycles of 16 hours of light and 8 hours of dark as this cycle produces the greatest number of embryos.

The culturing of immature embryos from somatic cells derived from explants may involve growth of sub-cultures from the initial culture. Most preferably initial culture is maintained for at least three months on the initial medium before subculturing to fresh media. This has been found to produce the optimal number of embryogenic cultures.

Where the initial culture of explant involves the initiation of embryogenic callus from explants on solid media, step 1 of the method of the present invention further involves the subculturing of embryogenic callus from the explant in liquid media to establish and maintain embryogenic cell suspension cultures. Up until the present invention, such sub-culturing presented numerous problems which include extensive browning of the callus cultures when transferred to liquid medium, the production of a large number of roots rather than embryos in liquid culture, the aggregation of the callus cells rather than formation of a fine suspension culture etc.

Previously, the browning of the liquid culture medium was only prevented by repeatedly changing the culture medium every 3–5 days. Such changes are time consuming and can waste expensive medium. The medium changes can also introduce the possibility of culture contamination and loss of important chemicals produced by cells. Medium replacement to overcome browning problems is therefore not a practicable option for the large scale propagation of sugar cane via somatic embryogenesis. A different solution to this problem has been found by the present invention which does not require such repeated sub-culturing for the avoidance of browning.

In the present invention most preferably embryonic callus formed from root explant either alone or in combination with other types of explant is used to form the liquid suspension culture. Root callus disperses quickly and produces a fine suspension with minimal cell aggregates. Furthermore root callus substantially does not produce any medium or cell browning and thus suspension cultures of root callus do not require further sub culturing to avoid the problems of medium and/or cell browning. The method of the present invention using sugar cane root explant for culture is important for all types of plant culture which, up until the present invention have suffered from "browning" problems such as date palm.

At least in the case of leaf explant derived cultures ascorbic acid and citric acid assist in preventing browning of cells and culture media. Ascorbic acid is accordingly preferably included as a constituent of the callus initiation solid medium and the liquid embryogenic suspension medium. Different concentrations of ascorbic acid/citric acid are required at different stages of the culture process of the present invention. Most preferably in the initiation of callus from leaf explant approximately 1–2 mg/l of ascorbic acid is included in the solid media to prevent explant browning. For the initiation of suspension culture from callus, preferably 50 mg/l to 200 mg/l of ascorbic acid and most preferably approximately 100 mg/l of ascorbic acid together with preferably 250 mg/l of citric acid and most preferably approximately 150 mg/l of citric acid is included in the media. After the initial stage of suspension culture, a concentration of 2 mg/l to 20 mg/l and most preferably approximately 10 mg/l of ascorbic acid should be present in the maintenance medium to avoid browning.

Other anti-oxidants may be useful for example, activated charcoal may be incorporated in the initial solid medium before the callus is transferred to liquid media to initiate the suspension culture.

Alternatively both root and non-root explants are cultured together, as the presence of the root explant/callus substantially inhibits the occurrence of medium and cell browning.

An important factor influencing the formation of suspension cultures and their subsequent growth is the density of callus inoculum. The higher the density of inoculum the higher the frequency of cell aggregation. To obtain finely dispersed suspension culture, preferably the inoculum density is in the range 1–10 g/l of medium. Most preferably the density is approximately 5 g/l.

Most preferably the photoperiod for optimal growth of the suspension culture is 16 hours light/8 hour dark cycles.

Most preferably the carbohydrate source in the liquid culture media is sucrose. It may of course be other types of carbohydrate such as the above mentioned mono-and di-saccharides. For optimal embryo production, most preferably a sucrose and/or glucose concentration of 20 to 60 g/l and most preferably approximately 30 g/l is used.

Preferably abscissic acid (ABA) is included in the liquid media. A concentration of between 0.1 and 20 mg/l is preferred and most preferably approximately 1 mg/l is preferable as this suppresses the growth of non-embryogenic cells whilst encouraging the growth of embryogenic cells, promoting the production of a substantially pure embryonic culture. This is particularly advantageous for efficient long term maintenance of the embryogenic culture as it avoids the need for the labour intensive removal of the non-embryogenic cells formed during each sub-culture to ensure efficient long-term regeneration. This use of ABA in culture media for the inhibition of growth of non-embryogenic cells could also be important in the culture of other types of plants.

For commercial large scale propagation of sugar cane embryos it is preferred, where the explant derived callus is initially grown on solid media for it to be transferred for further development in liquid culture. If the explant derived callus grown initially on solid media continues development on solid media the embryos do not develop synchronously and have to be individually handled, although they will eventually become established as sugar cane plantlets. Accordingly for commercial large scale propagation of sugar cane, it is preferable for the explant derived callus to be transferred from the solid media to liquid suspension culture for further development. However, importantly, it is alternatively possible to initiate immature globular embryo production directly from root-explants directly in liquid suspension culture avoiding the need for initial induction on solid media as required for example for at least shoot and leaf explant culture.

Step 2 of the method of the present invention accordingly most preferably involves the maturation of the immature globular embryos in liquid phase suspension culture to fully developed embryos by induction of somatic embryogenesis. Up until the present invention problems have prevented the successful production of mature sugar cane embryos in liquid culture.

The present invention provides a method of successfully achieving this using root, shoot and leaf explants as the initial plant tissue source. Most preferably root explants are used. Avantageously root-derived cultures in step 2 produce a mucilaginous material which renders the suspension viscous. This mucilaginous material has important properties which assist in prevention of browning. Furthermore the increased viscosity of the culture medium increases the degree of embryogenesis. Production of the mucilaginous material could be induced from sugar cane roots by submerging the roots in water at a relatively high temperature (such as 35° C.) in sterile conditions. The mucilaginous material may then be retrieved and added to any plant tissue/cell culture suffering from "browning". The use of this material could replace the need for including expensive antioxidants in culture media normally required to avoid "browning".

As hereinbefore described, sugar cane immature embryos are effectively induced from explants in media comprising 2,4-D. Most preferably, for step 2 the immature embryos are subsequently transferred to a liquid medium free of 2,4-D auxin to encourage development of mature embryos. However, only root-derived suspension culture develops mature embryos in the liquid 2,4-D free media substantially without browning. Where leaf and shoot-derived suspension cultures, for example, are transferred to 2,4-D free media, browning develops which reduces the maturation of embryos. Accordingly, in such circumstances it is preferable to add activated charcoal or other suitable anti-oxidants at this stage to the media which assists in controlling browning of media and cells to allow and encourage mature embryos to develop. The addition of activated carbon/anti-oxidants is not a requirement for root-derived cultures but may be included in certain circumstances for example, when the root culture is older than approximately two months because beyond that time the root culture typically starts suffering from the problems of "browning". Most preferably, where activated charcoal is required it is added to the liquid media at a concentration of approximately 3 g/l.

Preferably the culture is allowed to develop over a period of time, preferably for between 50 and 60 days. During the maturation period preferably the media is changed frequently, for example weekly. The somatic embryogenesis of the immature globular embryos to bipolar and then to mature somatic torpedo embryos occurs in approximately 30–40 days depending on culture conditions, for example.

For somatic embryogenesis to be used for the large scale production of sugar cane plants, the mature embryos which are delivered to the field (preferably in the form of synthetic seeds) should produce a uniform growth of plants to facilitate agricultural operations such as weeding, irrigation and harvesting. In the case of sugar cane, plants must be at a certain age of maturity in order to achieve maximum sugar production. The sugar yield is reduced dramatically after flowering. It is therefore critical to have all the mature embryos for subsequent germination at the same stage of development so that the plants mature at the same time.

In order to avoid asynchronous maturation of the immature embryos, most preferably step 2 comprises a method of treating the embryos to overcome asynchronous development. Suitable treatments include storing the suspension culture in cold storage. Optimal conditions are for example, storage at 5° C. (+ or −1° C.) for approximately 10 days. A further simple treatment which advantageously is easy to apply in situ without risk of contamination is heat treatment, for example at approximately 50° C. for 45–60 mins. After this treatment non-embryogenic and embryogenic cells loose their viability whereas embryos are unaffected.

Following this heat treatment, or alternatively, preferably the suspension culture is sieved as described above in relation to the first step of the present invention in order to select for a culture having a higher percentage of somatic embryos. Optimally the suspension is sieved through a 63 $\mu$m mesh first sieve and collected on a 45 $\mu$m mesh second sieve.

Optimally, following sieving, the culture is agitated which substantially removes any remaining non-embryogenic cells. When the culture is within a stirred bioreactor this agitation is conveniently achieved by operating the stirrer at approximately 500 rpm for approximately 1 hour. It will be appreciated that the above methods of optimizing synchronous development of embryos in culture may be advantageously utilised for any type of plant culture where asynchronous development generally occurs for example in the culture of embryos for the production of trees, date palm and potato.

The production of sugar cane somatic embryos using bioreactors is highly desirable for the mass propagation of sugar cane plants by tissue and cell culture. Using a bioreactor, it is possible to control the culture conditions, automate the method, produce large volumes of suspension cultures and avoid the need to subculture the suspension cultures produced.

Bioreactors have many advantages over shake flasks for somatic embryogenesis. Apart from their large working volume, bioreactors provide a homogeneous culture because of the mixing produced by either mechanical stirring or by the aeration of the medium. Using bioreactors, it is possible to monitor pH, dissolved oxygen concentration and other environmental factors.

One of the most important factors is the dissolved oxygen concentration in the medium which is controlled by the rate of aeration and agitation in the bioreactor. Other factors of importance are the distribution and density of cells within the medium.

Any type of bioreactor is suitable for the method of the present invention such as air-lift bioreactors and mechanically stirred bioreactors. In an air-lift bioreactor air is used both to supply the aeration and to mix the culture. With the mechanically stirred bioreactor, it is possible to control the oxygenation of the medium independently of the level of mixing. This latter type of bioreactor is accordingly preferable as it is possible independently to vary the rotational speed of the mechanical stirrer. None of the non-embryogenic cells survive at rotor speeds in excess of 500 rpm so that variation of rotor speed is a valuable means of improving the synchrony of an embryogenic culture.

The percentage of somatic embryogenesis in the stirred-tank bioreactor is generally higher than that in the air-lift bioreactor. The stirred tank provides good mixing at all the stages whereas the flow rate in the air-lift bioreactor has to be increased continuously with increasing growth because many of the cells settle if the rate of air-flow is low. Considerable evaporation and froth formation occurred with high airflow rates which causes many cells to be attached to the wall of the bioreactor.

According to a further aspect of the present invention there is provided a method for the culture of sugar cane mature somatic embryos from immature embryos comprising the steps of:

(1) preparation of immature embryo liquid suspension culture from explant (2) culturing the suspension in a bioreactor to form somatic embryos.

Most preferably the culture of step (1) and step (2) occurs in a bioreactor. However, step (1) could alternatively occur for example, in a shake flask and the immature embryo culture used as an innoculum for culture in a bioreactor in step (2).

Most preferably step (1) comprises direct culturing of root embryonic callus from a root explant in media comprising 2,4-D and ABA. Optimally the concentration of 2,4-D is in the range 0.1 to 5 mg/l and most preferably 3 mg/l and the concentration of ABA is optimally 0.1 to 20 mg/l and most preferably 1 mg/l. Preferably prior to step (2) the method comprises sieving the culture through a sieve to form a fine suspension in the above described manner. Preferably the sieve mesh size is 63 $\mu$m and the suspension is collected on 45 $\mu$m mesh size sieve, which substantially ensures that the fine suspension substantially comprises somatic cells. Subsequently the method preferably comprises an additional step of resuspending the culture of step 1 in fresh media prior to step 2. That additional step preferably comprises sub-culturing in a fresh media comprising 2,4-D and ABA for optimally approximately 1 month to form a highly embryonic culture. Most preferably the density of inoculation for resuspension in a bioreactor is approximately 5 g/l. Any non-embryogenic cells remaining are most preferably removed by agitation of the culture at 500 rpm for 1 hour. This is most conveniently achieved in a stirred-tank type of bioreactor where the rotor speed of the stirrer can be adjusted accordingly.

Step (2) preferably comprises culturing the suspension in 2,4-D free medium comprising ABA, preferably in a stirred bioreactor. Most preferably the media in the bioreactor are regularly replaced until maturation occurs. This generally occurs in approximately 50 days. Preferably the media are replaced for example, every 10 days.

The mature embryos produced by the method of the present invention (in a bioreactor or otherwise) may subsequently be encapsulated to form "artificial seeds".

The production of sugar cane plantlets comprises the maturation of somatic embryos to plant seedlings by germination of the embryos. Most preferably this step comprises the culture of individual somatic embryos in liquid media. Preferably this culturing occurs on polythene foam. Polythene foam advantageously supports the seedlings allowing easy direct transfer of the seedling to the field. Preferably the somatic embryos are at a late torpedo stage. The embryos are preferably cultured in liquid 2,4-D free media. The media may advantageously include ABA at a concentration of 0.05–1 mg/l and most preferably 0.1 mg/l. The seedlings produced from embryos treated with ABA are found to be more vigorous and survive better in greenhouse conditions.

The somatic embryos produced by the method of the present invention may be encapsulated to form an artificial seed prior to their germination.

According to a further aspect of the present invention there is provided a method for encapsulating a somatic embryo comprising the step of adding at least one encapsulating agent to a somatic embryo. The method is suitable for the encapsulation of many plant somatic embryos including, but not limited to, sugar cane, all types of trees, potatoes, date palm etc. to form so-called "artificial seeds" which are easy to handle, store and transport.

Most preferably the encapsulating agent comprises at least a whole cereal flour/water paste. Such a paste as an encapsulating agent is particularly advantageous since it provides nutrients for the enclosed embryo, allows aeration of the embryo, forms a crust to keep the embryo moist and easy germination for the embryo yet is inexpensive. Whole sorghum flour is a particularly preferred agent since it is particularly inexpensive. The flour used could be fermented or non-fermented. Fermented flour is most preferable since the capsules produced therefrom are substantially resistant to cracking. The flour to water mix is preferably 5–30 g flour per 100 ml water and is most preferably approximately 10 g of flour to 100 ml of water.

The method of encapsulation preferably comprises the steps of:

(1) forming a flour/water paste
(2) adding somatic embryos to the paste
(3) placing individual embryos encapsulated in paste into water to form a capsule around the or each embryo
(4) drying the capsule The method of forming the flour/water paste preferably comprises mixing the flour and water together, heating the mixture to form a paste, autoclaving the paste, cooling the paste.

Prior to drying, the capsule could be dipped in a microbiocidal agent such as a fungicide and/or bacteriocide.

Before or after step (4) of the method of encapsulating the embryo the method could further comprise the steps of:

(a) adding sodium alginate solution to the capsule
(b) subsequently placing the capsule in calcium chloride solution.

Those additional steps produce beads of calcium alginate containing single embryos encapsulated in a flour paste.

Optimally, the concentration of sodium alginate solution used in the above mentioned step is approximately 3% which is transferred to, optimally, a 75 mM solution of calcium chloride in step (ii). The beads of calcium alginate containing a single embryo may be allowed to germinate in liquid or solid media such as 2,4-D free media or directly in soil.

According to a further aspect of this invention there is provided an artificial seed comprising a plant embryo encapsulated in a flour-based material. Preferably the flour-encapsulated embryo is enclosed within a calcium alginate bead. Most preferably the artificial seed is produced by the above described method. Most preferably the plant embryo is a sugar cane somatic embryo produced by the method of the present invention.

Such artificial seeds comprising somatic embryos provide numerous advantages over sexual seeds. For example, a higher rate of germination occurs than with sexual seeds. Furthermore the artificial seeds are genetically stable and highly viable in contrast with the chromosomal variation and poor viability typically exhibited by sexual seeds. Furthermore, such artificial seeds provide numerous advantages over vegetive propogation of sugar cane which is costly in terms of sugar cane usage, labour and transport and also carries a high risk of disease contamination. The method of producing somatic embryos and subsequent encapsulation to form artificial seeds of the present invention provides a highly efficient method of sugar cane production as it provides a contamination free, low labour, time efficient method for the mass-production of viable genetically identical artificial seeds from a single sugar cane explant. The artificial seeds produced may be stored, transported and planted at minimal costs.

The plants produced by vegetative propagation of a mother plant are similar in morphology, sugar content, biochemistry etc as those produced by somatic embryogenesis in accordance with the present invention, and furthermore the plants produced by the method of the present invention are similar to the original mother plant in a wide variety of characteristics. Accordingly the method of the present invention provides a commercially important and viable new method for the large scale production of sugar cane.

According to a further aspect of the present invention there is provided sugar cane somatic embryos produced by a method comprising the steps of:

(1) culturing immature embryos from explants
(2) culturing mature sugar cane somatic embryos from those immature embryos According to a further aspect of the present invention there is provided a sugar cane plant produced by a method comprising the steps of:

(1) culturing immature embryos from explants
(2) culturing mature sugar cane somatic embryos from those immature embryos
(3) germinating those somatic embryos to form at least one sugar cane plant.

Most preferably that method includes an additional step prior to step 3 of encapsulating the mature somatic embryos produced in step 2 in encapsulating agent(s). Preferably the sugar cane somatic embryos are produced by a method in accordance with the above described aspects of the present invention.

Preferably hose steps comprise a method in accordance with the above described aspects of the present invention.

The present invention will now be described by way of the following non-limiting examples.

EXAMPLES

Preparation of Leaf Explants

Sugar cane setts from variety Co527 (Kenana Sugar Company) were immersed in a water bath at 52° C. for 2 days to expose any contamination and promote rooting and shooting.

The setts were subsequently grown on Levington Multi-purpose Compost (Fisons) at 25° C. with a 16 hour light photoperiod in a glasshouse from November to April and using natural daylight from May to October.

The growing plants were fertilized weekly with liquid fertilizer (Tomorite Rey TM, Fisons).

Leaf explants were excised at three months as 5 mm segments of outer and inner leaves.

The leaf explants were sterilized by soaking in 95% ethanol for 20 mins.

Preparation of Shoot or Root Explants

Plantlets are obtained in vitro from a callus culture initiated from a leaf explant (variety Co527). A mother plant was selected from those plantlets and propagated on shoot multiplication medium. Root and shoot explants were obtained from such three month old micro-propagated plants. The root and shoot explant were transferred from regenerated plants in axenic cultures without sterilization.

Preparation of Culture MS (Murashinge and Skoog, 1962) Medium

The basic medium was prepared from stock solutions and then supplemented with various combinations of plant growth regulators, vitamins and sugars, stock solutions of which were prepared separately and stored at −20° C. in dark bottles. Myo-inosiltol, solidifying agent (agar) and carbohydrates were added to the media during preparation. The media were made up with double distilled water. Heat-stable plant growth regulators as well as other compounds were added before autoclaving, while heat labile compounds such as zeatin and ABA were added to the lukewarm media just before pouring into the sterile plates. All media were adjusted to pH 5.8 by using 1M MaOH or 1M HCl prior to autoclaving. In the case of the solid medium, 0.9% (w/v) agar (Sigma, UK) was added before adjustment of the pH.

Murashige and Skoog (1962) medium with 30 g/l sucrose and 3 mg/l 2,4-D was used for the growth and maintenance of the callus cultures, suspension cultures in shake flasks and bioreactors; it is referred to as (MS1). For Embryogenesis, Murashige and Skoog medium with 30 g/l sucrose was used and referred to as (MS2). Adjustments to the media may be made as required.

Periodic samples were taken aseptically and smeared onto plates of MYGP agar (malt and yeast extract, glucose and peptone), PDA (potato dextrose agar) and NA (nutrient agar) all supplied by Oxoid, Basingstoke, Hants. These plants were then incubated for 1 week at 25° C. before being checked for microbial growth.

Initiation of Callus Cultures

Callus cultures were initiated by culturing explants in 90×15 mm sterile plastic Petri dishes (Sterilin Ltd. UK) containing MS1 solidified with 0.9% agar. The Petri dishes were sealed with parafilm (American National Can Co.) to reduce loss of moisture by evaporation. After several weeks of incubation, when callus had grown, it was removed with sterile forceps and placed on fresh agar plates. These were then incubated for a further month. The remaining original explants, including any dark brown or contaminated tissues were discarded.

Production of Suspension Cultures

Suspension cultures were initially produced by placing 0.5–1.0 g (fresh weight) of callus material into sterile 250 ml Erlenmeyer shake flasks (Corning, Stone, Staffs.) containing 50 ml of MS1, After resealing with a double layer of sterilised aluminium foil squares of about 12×12 cm, the flasks were placed on rotary shakers at 100 rpm. Over several weeks, this gentle shaking action encouraged smaller fragments of cells and single cells to separate from the larger aggregates. The cultures were then sub-cultured, particular care being taken to transfer the smaller lumps and discard the larger aggregates. Aliquots of 10–15 ml of the finer cell aggregates were transferred to 50 ml fresh medium in 250 ml shake flasks every week.

Direct Initiation of Root Suspension Culture for Small Scale Production

Roots either harvested from mature plants or from micro-propagated plants were put directly into liquid medium which contains 0.5–10 mg/l 2,4-D (most preferably 3 mg/l), and ABA 0.1–10 mg/l (most preferably 1 mg/l). A fine suspension culture is formed.

Production of Mature Embryos by Somatic Embryogenesis

For embryogenesis, cultures were transferred to MS medium free of 2,4-D. Maturation of embryos occurred in the same MS medium without growth regulators.

Initiation of Root Suspension for Industrial Use (as Inoculum for Large Bioreactors)

A well reared mother plant at the age of nine months is the source of the plant material. The plant was cut 10 cm above the ground a set with two nodes (about 20 cm long) was excised, the cut ends was waxed using a melted paraffin wax. The sett was sterilised in 20% sodium hypochlorite for 20 minutes and washed many times with distilled water, the waxed ends were removed. The buds were carefully removed to inhibit the growth of the shoots inside the bioreactor. The plant was placed inside a three litre bioreactor adjacent to the bioreactor wall and held to the wall by round silicon tube attached to the wall by means of non-toxic glue.

The bioreactor was filed with distilled water and the temperature was controlled by means of water-bath at 35° C. with out running the stirrer. A massive root network grew. When the roots were approximately 1 inch long, the distilled water was siphoned out and the bioreactor was filled with MS1 medium. The temperature is subsequently reduced to 27° C. The bioreactor was stirred at 100 rpm. After 1 month a fine suspension free of browning was ready to be used as inoculum.

The fine suspension was sieved though 63 $\mu$m mesh sieve and collected on size 45 $\mu$m mesh sieve.

Production of Somatic Embryos in 5 Litres Bioreactor for Commercial Use

From the above inoculum 25 g of cells was used to inoculate 5 litres stirred-tank bioreactor using MS2 medium. The stirrer was operated at 500 rpm which removed any non-embryogenic cells remaining. This procedure resulted in highly synchronized growth. At the end of the run 93% of the embryos were torpedo embryos at a density of approximately 1 million embryo per litre.

Production of Encapsulated Somatic Embryos

Sorghum flour (10 g) was mixed with water (100 ml) and the pH was adjusted to 5.8. The mixture was brought to boiling while continuously stirring to form a thick paste (it immediately solidified when a drop placed in water). At this stage the paste was autoclaved, at 15 psi, 121° C. for 20 minutes. The paste was cooled to 40° C. For encapsulation, mature embryos were picked from the maturation medium after 3 weeks and then embryos were singly dropped in the paste. Using a pipette a rounded capsule comprising an embryo encapsulating the paste was dropped in cold water. At this stage the capsule could be dipped in fungicide and bactericide. Then the capsules were dried.

Sodium alginate (Sigma) was added at concentration 3.0,% (w/v) to MS2. The medium was autoclaved after adjusting the pH to 5.8. Flour-encapsulated embryos were first individually dipped in the sterile sodium alginate solution and then dropped in 75 mM calcium chloride solution in a beaker placed on a magnetic stirrer. The resultant beads, each containing a single somatic embryo were recovered by decanting the calcium chloride solution and washing with MS liquid medium.

Germination of Embryos to Produce Plantlets

After germination in MS (solid or liquid) medium, seedlings were transferred to perlite and then Levington compost (after 3 weeks) and grown on in a green house at 15–32° C. and 87% relative humidity. Long day conditions (16 hours light) were maintained under mercury vapour lamps. After 3 weeks, the plantlets were transferred to compost).

Viability Test

Viability of cells and embryos in culture was assessed using the fluorescein diacetate (FDA) test (Widholm, 1972). A solution of FDA in acetone (5 mg/ml) was diluted in water to give a final concentration of 0.01% before use. Equal volumes of this solution and the cell suspension were mixed and left at room temperature for at least 3 minutes. One drop of the mixture was pipetted onto a glass microscope slide, covered with a glass coverslip and viewed under an Olympus BH2 U.V. microscope fitted with a model BH-RFL-W reflected light fluorescence attachment, 100 watt mercury vapour lamp, EY0.455 exciter filter, B(DM0.500+0.515) dichromatic mirror and a 530 nm barrier filter. After several minutes to allow the fluorescent to develop, tile numbers of yellow-green fluorescing cells (viable) and the total number of cells including non-fluoresencing (non-viable) cells were counted in 10 random fields.).

It will be appreciated by those skilled in the art that the present invention provides a time and labour efficient, yet reliable method suitable for the large scale production of sugar cane mature embryos. Advantageously the method is suitable for production to occur in a bioreactor where the method may be fully automated.

It is to be understood that the scope of the invention should not be limited to the above described examples, as those examples are for illustration by way of example only.

What is claimed is:

1. A method of production of mature sugar cane somatic embryos from sugar cane explants comprising the steps of:
   (1) culturing immature embryos from explant material;
   (2) culturing mature sugar cane somatic embryos from those immature embryos, and characterised in that at least step (2) occurs in liquid suspension culture in culture medium.

2. A method according to claim 1 characterised in that both of steps (1) and (2) occur in liquid suspension culture in culture medium.

3. A method according to either of claims 1 or 2 characterised in that the sugar cane explants are derived from characteristic organised meristems or meristematic cells of sugar cane plants.

4. A method according to claim 1 characterised in that the explants comprise root explants.

5. A method according to claim 4 characterised in that the explants are subjected to stressing.

6. A method according to claim 5 characterised in that stressing is achieved by cooling the explants.

7. A method according to claim 6 characterised in that the explants are cooled to 5–15° C. for 1–3 months.

8. A method according to claim 5 characterised in that stressing is achieved by treatment with alcohol.

9. A method according to claim 1 characterised in that the method of culturing immature embryos from explants (step 1) comprises the steps of:
   a) culturing explants in culture medium to produce somatic cells;
   b) selecting and multiplying somatic cells derived from the explants;
   c) culturing the somatic cells for a period of time in culture medium to induce immature sugar cane embryos from the somatic cells.

10. A method according to claim 1 characterised in that the immature embryos are derived from embryogenic callus on solid medium or from an embryogenic cell suspension cultured in liquid media or in a combination of both solid and liquid medium.

11. A method according to claim 1 characterised in that a plant growth regulator selected from the group consisting of an auxin, a cytokinin, a gibberellin, abscissic acid, an anti-auxin, kinetin, zeatin and activated charcoal is included either alone or in combination in the culture medium.

12. A method according to claim 1 characterised in that said method is performed in a culture medium containing sucrose.

13. A method according to claim 12 characterised in that the concentration of sucrose used is in the range of 10–60 g/l.

14. A method according to claim 1 characterised in that the explants are derived from sugar cane plant tissue having exposed cut ends coated with wax.

15. A method according to claim 1 characterised in that step (1) includes treatment to select for somatic embryos, said treatment comprising stirring of the liquid suspension culture.

16. A method according to claim 15 using a first sieve of 100–50 µm mesh size and subsequently a second sieve having a mesh size of 50–38 µm.

17. A method according to claim 1 characterised by the use of light and dark cycles during production of the immature embryos.

18. A method according to claim 1 characterised in that the culturing of immature embryos comprises sub-culturing the immature embryos of step (1) using fresh culture medium for the sub-culture.

19. A method according to claim 1 characterised in that the production of sugar cane mature somatic embryos from immature embryos comprises the steps of:
   (1) preparation of an immature embryo liquid suspension culture from explants;
   (2) culturing the liquid suspension culture in a bioreactor to form mature somatic embryos.

20. A method according to claim 19 characterised in that the culture of step (1) as well as step (2) occurs in a bioreactor.

21. A method according to claim 1 characterised in that mature embryos produced are encapsulated with an encapsulating agent prior to their germination.

22. A method according to claim 21 characterised in that the encapsulating agent comprises a paste formed from cereal flour and water.

23. A method according to claim 22 characterised in that the flour is sorghum flour.

24. A method according to claim 21 characterised in that encapsulation comprises the steps of:
   (1) forming a paste of flour and water;
   (2) adding somatic embryos to the paste;
   (3) placing individual embryos encapsulated in paste into water to form a capsule around the embryo(s) to form a flour-encapsulated embryo; and
   (4) drying the encapsulated to form a mature embryo encapsulated with an encapsulating agent.

25. A method according to claim 24 characterised in that prior to drying (step (4)) the capsule is dipped in a microbiocidal agent.

26. A method according to claim 24 characterised in that prior to drying (step (4)) encapsulation of the embryo further comprises the steps of:
   a) Contacting the flour-encapsulated embryo with a sodium alginate solution to form an alginate-treated, flour-encapsulated embryo;
   b) Contacting the alginate-treated, flour-encapsulated embryo with a calcium chloride solution.

27. A method according to claim 1 characterised in that the method further comprises the step of producing sugar cane seedlings through germination of mature sugar cane somatic embryos carried on polythene foam in liquid medium.

28. A method according to claim 27 characterised in that the mature somatic embryos are cultured in 2,4-D auxin free liquid medium and this liquid medium includes abscissic acid.

29. A method according to claim 1 characterised in that at least step (1) is carried out using culture medium containing an antioxidant.

30. A method according to claim 29 characterised in that both of steps (1) and (2) are carried out using culture medium containing an antioxidant.

31. A method according to either of claims 29 or 30 characterised in that the antioxidant comprises at least one of ascorbic acid and citric acid.

32. A method according to claim 1 characterized in that the culture of immature embryos from explants initially involves initiation of embryogenic callus from the explants on solid medium followed by sub-culturing of embryogenic callus in liquid medium to establish and maintain embryogenic cell suspension cultures.

33. A method according to claim 32 characterised in that the initiation of embryogenic callus from the explants is carried out on solid medium containing approximately 1–2 mg/l of ascorbic acid.

34. A method according to claim 32 characterised in that the embryogenic cell suspension cultures are established in liquid medium containing 50 mg/l to 200 mg/l of ascorbic acid and subsequently maintained in liquid medium containing 2 mg/l to 20 mg/l of ascorbic acid.

35. A method according to claim 34 characterised in that the embryogenic cell suspension cultures are established in liquid medium further containing approximately 150 mg/l of citric acid.

36. A method according to claim 1 characterised in that at least step (1) is carried out using culture medium containing abscissic acid.

37. A method according to claim 36 characterised in that step (1) is carried out using culture medium further containing an auxin.

38. A method according to claim 37 characterised in that the auxin is 2,4-D auxin.

39. A method according to claim 38 characterised in that abscissic acid is present at a concentration of between 0.1–20 mg/l and 2,4-D auxin is present at a concentration of between 0.5–10 mg/l.

40. A method of production of sugar cane somatic embryos from sugar cane root explants comprising the steps of:
   (1) culturing immature embryos from root explants; and
   (2) culturing mature sugar cane somatic embryos from those immature embryos,
   (3) and characterised in that the method results in the production of a mucilaginous material, said production being induced by submerging the root explants in water at a temperature of above room temperature in sterile conditions.

41. A method according to claim 40 characterised in that temperature is approximately 35° C.

42. A method according to claim 40 characterised in that step (2) includes transfer of the immature embryos to a liquid medium substantially free of 2,4-D auxin.

43. A method according to claim 1 characterised in that the immature embryos of step (2) are transferred to 2,4-D auxin-free medium containing activated charcoal or other antioxidant.

44. A method of production of sugar cane somatic embryos from sugar cane explants comprising the steps of:
   (1) culturing immature embryos from explants; and
   (2) culturing mature sugar cane somatic embryos from those immature embryos, and characterised in that at least step (2) occurs in liquid suspension culture in culture medium; step (1) is carried out in the presence of at least one growth regulator active to induce immature embryo formation; at least step (1) is carried out in the presence of a growth regulator active to retard the growth of non-embryogenic cells; and at least step (1) is carried out in the presence of at least one antioxidant.

45. A method according to claim 44 characterised in that the growth regulator active to induce immature embryo development comprises an auxin.

46. A method according to claim 45 characterised in that the auxin is 2,4-D auxin.

47. A method according to claim 44 characterised in that the growth regulator active to retard the growth of non-embryogenic cells is selected from abscissic acid and anti-auxins.

48. A method according to claim 44 characterised in that the antioxidant comprises at least one of ascorbic acid, citric acid, activated charcoal and a mucilaginous material obtained from sugar cane roots by submerging the roots in water at a temperature of approximately 35° C.

49. A method according to claim 25 characterised in that the microbiocidal agent comprises at least one agent selected from the group consisting of fungicides and bacteriocides.

* * * * *